United States Patent [19]

Gehrke et al.

[11] Patent Number: 5,286,847
[45] Date of Patent: Feb. 15, 1994

[54] INTERLEUKIN-1 MUTEINS, THEIR PREPARATION AND METHOD OF USE TO INHIBIT INTERLEUKIN-1 ACTIVITY

[75] Inventors: Lee Gehrke, Framingham; Philip E. Auron, Ashland; Lanny Rosenwasser, Weston, all of Mass.

[73] Assignees: New England Medical Center Hospitals, Inc., Boston; Massachusetts Institute of Technology, Cambridge, both of Mass.

[21] Appl. No.: 887,118

[22] Filed: May 19, 1992

Related U.S. Application Data

[63] Continuation of Ser. No. 316,278, Feb. 27, 1989, abandoned.

[51] Int. Cl.$^5$ .............................................. C07K 13/00
[52] U.S. Cl. ..................... 530/351; 424/85.1; 424/85.2; 435/69.5; 435/69.52; 930/141
[58] Field of Search ........... 530/351; 435/69.5, 69.52; 424/85.1, 85.2; 514/2, 8, 21; 930/141

[56] References Cited

U.S. PATENT DOCUMENTS

| | | | |
|---|---|---|---|
| 5,008,374 | 4/1991 | Nakai et al. | 530/351 |
| 5,039,790 | 8/1991 | Adams et al. | 424/85.2 |
| 5,047,505 | 9/1991 | Huany | 530/351 |

FOREIGN PATENT DOCUMENTS

| | | |
|---|---|---|
| 0237073 | 9/1987 | European Pat. Off. . |
| 0237967 | 9/1987 | European Pat. Off. . |

OTHER PUBLICATIONS

Wingfield et al., *FEB* 1987 pp. 160–164.
Kamagashira et al. *J. Biochem* 104, 1988, pp. 837–840.
Zurawaki et al., *Gene* 49, 1986, pp. 61–68.
Wells et al., *Gene* 34, 1985, pp. 3115–3123.
Lillquist et al., *J. Immunol* 141, 1988, pp. 1975–1981.
Dalszyaki et al., *Biochem Biophys Res Comm* 147, 1987, pp. 204–211.
Wingfield et al., *Protein Engineering* 1987, pp. 413–417.
Ferreira et al., *Nature*, 334, 1988, pp. 698–700.
Chemical Abstracts, vol. 108, No. 1, Jan. 4, 1988, (Columbus, Ohio, US) Huang, James J. et al.: "Muteins of human interleukin-1 that show enhanced bioactivities", see p. 438, abstract 4497p, FEBS Lett 1987, 223 (2), 294–298.
Auron, P. E., L. J. Rosinwasser, K. Matsushima, T. Copeland, C. A. Dinarello, J. J. Oppenheim, and A. C. Webb (1985) "Human and murine interleukin 1 possess sequence and structural similarities," J. Mol. Cell. Immunol. 2:169–177.
Webb, A. C., L. J. Roseswasser, P. E. Auron (1987) "Molecular organization and expression of the prointerleukin-1β gene," In: *Recombinant Lymphokines and Their Receptors*, S. Gillis, ed., Marcel Dekker, Inc., New York, pp. 139–158.
Dower, S. K., S. R. Kronheim, T. P. Hopp, M. Cantrell, M. Deeley, S. Gillis, C. S. Henney, and D. K. Urdal (1986) "The cell surface receptors for interleukin-1α are interleukin-1β and identical," Nature 324:266–268.
Kilian, P. L., K. L. Kaffka, A. S. Stern, D. Woehle, W. R. Benjamin, T. M. Dechiara, U. Gubler, J. J. Farrar, S. B. Mizel, and P. T. Lomedico (1986) "Interleukin 1α and interleukin 1β bind to the same receptor on T cells," J. Immunol. 136:4509–4514.
Sims, J. E., C. J. March, D. Cosman, M. B. Widmer, H. R. MacDonald, C. J. McMahan, C. E. Grubin, J. M. Wignal, J. L. Jackson, S. M. Call, D. Friend, A. R. Alpert, S. Gillis, D. L. Urdal, S. K. Dower (1988)

(List continued on next page.)

*Primary Examiner*—Garnette D. Draper
*Attorney, Agent, or Firm*—Saliwanchik & Saliwanchik

[57] ABSTRACT

Disclosed are novel muteins of IL-1 compounds which can be used to regulate excess IL-1 produced in various diseases in humans and animals. The IL-1 muteins can be prepared by site-directed mutagenesis whereby a positively charged residue is replaced with a negatively charged or neutral residue at a designated position in the molecule. The resulting IL-1 muteins have reduced biological activity but retain receptor binding affinity.

6 Claims, 4 Drawing Sheets

OTHER PUBLICATIONS

"cDNA expression cloning of the IL-1 receptor, a member of the immunoglobulin superfamily," Science 241:585–588.

Jobling, S. A., P. E. Auron, G. Gurka, A. C. Webb, B. McDonald, L. J. Rosenwasser, and L. Gehrke (1988) "Biological activity and receptor binding of human prointerleukin-1β," J. Bio. Chem. 263:16732–16738.

Auron, P. E., A. C. Webb, L. J. Rosenwasser, S. F. Mucci, A. Rich, S. M. Wolff, and C. A. Dinarello (1984) "Nucleotide sequence of human monocyte interleukin 1 precursor cDNA," Proc. Natl. Acad. Sci. USA 81:7907–7911.

Priesle, J. P., H. P. Schar, M. G. Grutter (1988) "Crystal structure of the cytokine interleukin-1β," EMBO J. 7:339–343.

DeChiara, T. M., D. Young, R. Semionow, A. S. Stern, C. B-. Bernardo, C. F.-. Nagy, K. L. Kaffka, P. L. Kilian, S. Yamazaki, S. B. Mizel, and P. T. Lomedico (1986) "Structure-function analysis of murine interleukin 1: Biologically active polypeptides are at least 127 amino acids long and are derived from the carboxyl terminus of a 270-amino acid precursor," Proc. Natl. Acad. Sci. USA 83:8303–8307.

Mosley, B., S. K. Dower, S. Gillis, D. Cosman (1987) "Determination of the minimum polypeptide lengths of the functionally active sites of human interleukins 1α and 1β," Proc. Natl. Acad. Sci. USA 84:4572–4576.

Huang, J. J., R. C. Newton, R. Horuk, J. B. Matthew, M. Covington, K. Pezzella, and Y. Lin (1987) "Muteins of human interleukin-1 that show enhanced bioactivities," FEBS Letters 223:294–298.

Gronenborn, A. M., P. T. Wingfield, H. F. McDonald, U. Schmeissner, G. M. Clore (1988) "Site directed mutants of human interleukin-1α: a H-NMR and receptor binding study," FEBS Letters 231:135–138.

MacDonald, H. R., P. Wingfield, U. Schmeissner, A. Shaw, G. M. Clore, and A. M. Gronenborn (1986) "Point nutations of human interleukin-1 with decreased receptor binding affinity," FEBS Letters 209:295–298.

INTERLEUKIN-1 MUTEINS, THEIR PREPARATION AND METHOD OF USE TO INHIBIT INTERLEUKIN-1 ACTIVITY

This invention was made with government support under NIH Grant No. GM42504. The government has certain rights in this invention.

This application is a continuation, of application Ser. No. 07/316,278, filed Feb. 27, 1989 now abandoned.

BACKGROUND OF THE INVENTION

Despite the fact that alpha- and beta-interleukin-1 molecules show limited amino acid homology (Auron, P. E. et al. [1985] J. Mol. Cell Immunol. 2:169–177; Webb, A. C., L. J. Rosenwasser, P. E. Auron [1987] In: *Recombinant Lymphokines and Their Receptors*, S. Gillis, ed., Marcel Dekker, Inc., New York, pp. 139–158), the proteins bind to the same membrane receptor protein (Dower, S. K. et al. [1986] Nature 324:266–268; Kilian, P. L. et al. [1986] J. Immunol. 136:4509–4514), which has recently been cloned (Sims, J. E. et al. [1988] Science 241:585–588). Human IL-1$\beta$ protein is synthesized as a 31,000 dalton precursor protein (proIL-1$\beta$; 269 amino acids) which binds receptor specifically and has relatively low, but distinct biological activity (Jobling, S. A. et al. [1988] J. Biol. Chem. 263:16732–16738). ProIL-1$\beta$ is processed by undefined mechanisms to generate the mature protein (IL1(1-17–269)), which has maximal biological activity. The numbering system used here is based upon the 269-amino acid unprocessed proIL-1$\beta$ precursor molecule (Jobling et al., 1988; Auron, P. E. et al. [1984] Proc. Natl. Acad. Sci. USA 81:7907–7911). The processed "mature" form of IL-1$\beta$ corresponds to positions 117–269. The crystal structure of human IL-1$\beta$ (Priestle, J. P., H. P. Schar, M. G. Grutter [1988] EMBO J. 7:339–343) has been described as a tetrahedron with edges formed by antiparallel $\beta$-strands, but the amino acids which interact with receptor have not been defined. It is very likely that the biological activity of IL-1$\beta$ is tightly linked to the structural integrity of the protein molecule, for deletion of amino acids from the mature protein is accompanied by severe diminution of bioactivity. Several groups have introduced point mutations in an attempt to probe receptor ligand interactions (Jobling et al., 1988; Dechiara, T. M. et al. [1986] Proc. Natl. Acad. Sci. USA 83:8303–8307; Mosley, B., S. K. Dower, S. Gillis, D. Cosman [1987] Proc. Natl. Acad Sci. USA 84:4572–4576). Huang et al. (Huang, J. J. et al. [1987] FEBS Letters 223:294–298) reported that the biological activity of IL-1$\beta$ was increased four- to seven-fold by changing the native NH$_2$-terminal sequence from ala-pro-val-arg-ser to thr-met-val-arg-ser; however, further alteration of arginine$_{120}$ to generate thr-met-val-glu-ser effectively abolished bioactivity. Circular dichroism data demonstrated no major structural differences among the proteins. Gronenborn et al. (Gronenborn, A. M., P. T. Wingfield, H. F. McDonald, U. Schmeissner, G. M. Clore [1988] FEBS Letters 231:135–138) mutated IL-1-alpha histidine and tryptophan residues without effect upon receptor binding affinity, while MacDonald et al. (MacDonald, H. R. et al. [1986] FEBS Letters 209:295–298) reported IL-1 histidine muteins with 2-100 fold less competitive binding activity than the wild-type protein. Although receptor binding affinity and bioactivity are, in general, correlated, the relationship is apparently not always direct.

BRIEF SUMMARY OF THE INVENTION

The subject invention concerns novel and useful muteins of IL-1. These muteins have reduced bioactivity, as compared to the parent molecule, without loss of receptor binding affinity. More specifically, the invention comprises IL-1 muteins wherein a positively charged residue (arginine or lysine) is replaced with any of the other 17 natural amino acids. The specific position of the IL-1 molecules at which this unexpected and dramatic change in biological activity occurs without affecting binding activity is as follows:

(1) Mature human IL-1$\beta$: position 11
(2) Human IL-1$\beta$ precursor (proIL-1$\beta$): position 127
(3) Position 131 in the human IL-1-alpha precursor, and any subpeptides thereof corresponding to a portion of the IL-1-alpha precursor and containing an amino acid corresponding to position 131. For example, position 19 in a mature form of human IL-1-alpha which starts with serine residue 113 in the precursor, or to position 13 in a mature form of human IL-1-alpha which starts with lysine residue 119 in the precursor. It should be noted that human IL-1-alpha precursor is processed in at least two different ways to generate subtly different biologically-active mature peptides (Cameron, P. M., G. Limjuco, J. Chin, L. Silberstein, and J. A. Schmidt [1986] J. Exp. Med. 164:237–250).

Specifically exemplified herein is the preparation and testing of a human proIL-1$\beta$ mutant wherein the mutant is prepared by site-directed mutagenesis of the IL-1$\beta$ cDNA to convert Arg$_{127}$ to Gly$_{127}$. The biological activity of the Arg$_{127}$→Gly$_{127}$ mutein is at least 100-fold less than the wild-type IL-1$\beta$. Equilibrium binding analyses and competitive binding studies demonstrate, however, that the receptor affinity of the Arg$_{127}$→Gly$_{127}$ mutant protein is indistinguishable from that of the wild-type IL-1$\beta$ protein. The Arg$_{127}$→Gly$_{127}$ mutant protein may be useful for the characterization of events which follow IL-1$\beta$ receptor-ligand interactions and lead to the multiple actions of the protein.

BRIEF DESCRIPTION OF THE DRAWINGS

FIG. 1. Schematic representation of human IL-1$\beta$ cDNA and deletion constructs. The interleukin-1$\beta$ cDNA was subcloned into plasmid pSP64 (Promega Biotec). The SP6 promoter is represented by the filled box, and the direction of transcription is noted by the horizontal arrow. The letter U symbolizes the untranslated leader sequence, which in these experiments was either the native IL-1$\beta$ sequence or that of alfalfa mosaic virus RNA 4. The open rectangle represents the IL-1$\beta$ precursor coding region, within which are shown regions of homology (a–e). Relevant restriction enzyme sites used to make the deletion constructs are shown above the IL-1$\beta$ sequence, and the location of the amino terminus of the processed mature IL-1$\beta$ protein (Ala$_{117}$) is denoted by the vertical arrow. Lower, schematic diagrams of the deletion constructs. Terminal amino acids are indicated by capital letters and subscript numbers (M, methionine; A; alanine; S; serine; H, histidine; L, leucine). Amino acids derived from vector sequence rather than the IL-1$\beta$ coding region are denoted by diagonal lines positioned at either end of the construct.

FIG. 2. Biological activities of IL-1$\beta$ proteins. Reticulocyte translation mixtures were incubated and assayed in the thymocyte co-stimulation assay as described previously (Jobling et al., 1988). The results are presented as [$^3$H]thymidine incorporation (counts/minute) at various final dilutions of the translation mixtures.

FIG. 3. Analysis of receptor binding. [$^{35}$S]-labeled IL-1β proteins were incubated at 4° C. with murine EL.4 cells in the absence (−) or presence (+) or non-radioactive competitor recombinant IL-1β protein. Following incubation, the cells were sedimented through silicone oil as described previously (Jobling et al., 1988). The IL-1β proteins are identified at the top of the figure by numbers corresponding to amino acid positions. IL1(1–269) is proIL-1β, while IL1(117–269) corresponds to the mature IL-1β protein. The "native" and "Gly$_{127}$" notations at the bottom of the figure refer to the wild-type mature protein (Arg$_{127}$) and the Arg$_{127}$→Gly$_{127}$ mutein, respectively.

FIG. 4. Competitive receptor binding. A constant amount of radioactive mature IL-1β protein was added to $1.9 \times 10^7$ EL.4 cells in binding medium. The results are presented as a percentage of radioactive IL-1β which bound specifically in the absence of competitor. The 100% value represents approximately 30,000 cpm.

DETAILED DESCRIPTION OF THE INVENTION

The conversion of IL-1 molecules by mutation of specific residues gives muteins having utility as IL-1 biological activity inhibitors. Specifically disclosed is the preparation and testing of human IL-1β. Table 1 shows that this mutant binds as efficiently as the native mature IL-1β protein (i.e., the protein derived from residues 117–269 of the precursor. IL-1β peptides were synthesized by in vitro translation of the presence of [$^{35}$S]methionine and incubated with EL.4 cells at 4° C. The equilibrium dissociation constants were determined by Scatchard plot analysis (Jobling et al., 1988). For comparison, the dissociation constants of proIL-1β and two IL-1β deletion constructs are also shown. The right column illustrates the receptor binding affinities expressed in relation to mature wild-type IL-1β (100%).

TABLE 1

| Dissociation constants and relative binding of IL-1β peptides. | | |
|---|---|---|
| Peptide | K$_d$ | Relative binding |
| mature IL-1β (117–269) | $1.01 \times 10^{-9}$ | 100 |
| mature Arg$_{12}$ → Gly$_{127}$ | $1.08 \times 10^{-9}$ | 107 |

Figure 2:
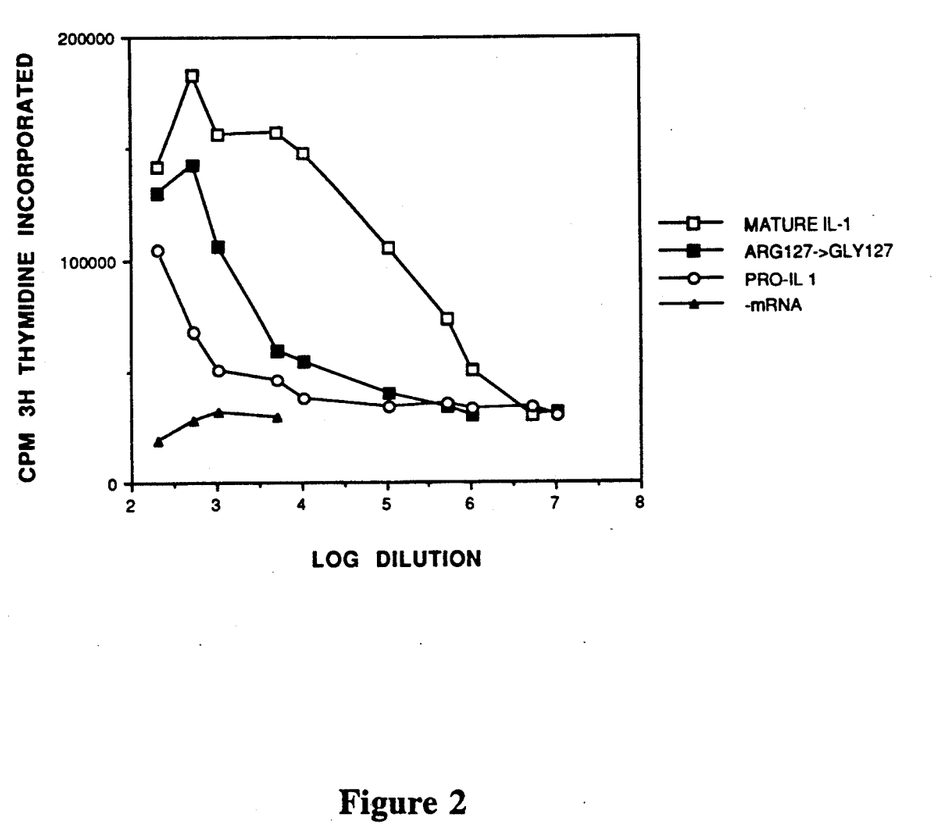

FIG. 2 shows that this same mutant induces only 1% of the biological activity induced by the mature IL-1β. The prediction that a protein with high receptor binding and low bioactivity should act as an inhibitor of IL-1 bioactivity is supported by the data in FIG. 4. Therefore, the substitution of a glycine for an arginine at position 127 of human IL-1β generates a novel molecule which binds to the IL-1 receptor without inducing a strong activity, thus interfering with the binding of active forms of IL-1.

Excessive or unregulated IL-1 has been implicated in various diseases. These include rheumatoid arthritis (See, e.g., Fontana et al. [1982] Arthritis Rheum. 22:49–53); osteoarthritis (See, e.g., Wood et al. [1983] Arthritis Rheum. 26:975); toxic shock syndrome (See, e.g., Ikejima and Dinarello [1985] J. Leukocyte Biology 37:714); other acute or chronic inflammatory disease states such as the inflammatory reaction induced by endotoxin (See, e.g., Habicht and Beck [1985] J. Leukocyte Biology 37:709); and other chronic inflammatory disease states such as tuberculosis (See, e.g., Chesque et al. [1985] J. Leukocyte Biology 37:690). Benjamin et al. ([1985] "Annual Reports in Medicinal Chemistry—20," Chapter 18, pp. 173–183, Academic Press, Inc.) disclose that excessive IL-1 production is implicated in Psoriatic arthritis, Reiter's syndrome, Rheumatoid arthritis, Osteoarthritis, Gout, Traumatic arthritis, Rubella arthritis, and Acute synovitis.

Dinarello ([1985] J. Clinical Immunol. 5(5):287–297) reviews the biological activities which have been attributed to IL-1. Thus, the IL-1 muteins of the invention can be used in treating, prophylactically or therapeutically, any disease state in a human or animal which is caused by excessive or unregulated IL-1.

Further, the invention includes IL-1 muteins from species other than human where a comparable residue can be mutated to produce IL-1 muteins with diminished biological activity but unaffected receptor binding activity. Such IL-1 muteins are useful as described above.

As disclosed above, the Arg$_{127}$→Gly$_{127}$ mutant form of IL-1β binds to the common IL-1 high affinity receptor with equal affinity as the fully active IL-1β (117–269), yet possesses a significantly reduced amount of biological activity. Thus, this mutant can be a comparative inhibitor for the effects of IL-1β. Since IL-1β is a potent stimulator of both immune and inflammatory reactions, the use of the novel invention as an anti-inflammatory, anti-immune agent is self evident.

For example, the Arg$_{127}$→Gly$_{127}$ IL-1β mutant can have general utility as an anti-inflammatory and anti-pyretic agent administered parenterally. Since circulating levels of IL-1 have been demonstrated in situations where there is infection, fever, and shock, the use of the Arg$_{127}$→Gly$_{127}$ mutant as an anti-pyretic and anti-inflammatory agent is self evident.

Also, the Arg$_{127}$→Gly$_{127}$ mutant of IL-1β can be used as an IL-1 inhibitor in the various forms of inflammatory arthritis that have been identified as containing IL-1 in synovial fluid. Among the inflammatory arthridities in which IL-1 has been demonstrated in joint fluid, there are rheumatoid arthritis, osteoarthritis, and gouty arthritis. It has been shown that synovial fluid in both rheumatoid arthritis and other forms contain bona fide IL-1β activity and that levels of this activity may be detected reliably as low as 50 pg/ml of IL-1β (Mc-Donald, B., L. Loose, and L. J. Rosenwasser [1988] Arthritis and Rheumatism 31 (Supp.):52; Saxne, T., G. W. Duff, G. DiGiovine, D. Heinegard, and F. A. Wollheim [1988] Arthritis and Rheumatism 31(Supp.):69). Thus, the intra-articular injection of a concentration of Arg$_{127}$→Gly$_{127}$ mutant of 5 ng/ml may be effective in turning off inflammatory arthritis.

Further, since IL-1β has been shown to be involved in the destruction of islet cells in diabetes mellitus (DM) (Mandrup-Paulsen, T., K. Bendtzen, J. Nerup, C. A. Dinarello, M. Svenson, and J. H. Nielson [1986] Diabetologia 29:63–67), it should be possible to use the Arg$_{127}$→Gly$_{127}$ mutant to limit lymphocyte and macrophage mediated damage to islet cells in incipient cases of DM identified by disease susceptibility via genetic background and family history. It may be possible to interdict inflammatory destruction of the pancreatic beta islet cells in such individuals with early DM with the use of parenterally administered Arg$_{127}$→Gly$_{123}$ mutant to generate a local concentration of Arg$_{127}$→

Gly$_{127}$ mutant that would have an anti-IL-1 effect in the pancreas.

Lastly, it is also possible to administer IL-1 muteins via airway inhalation in various forms of inflammatory airway disease of both the upper and lower airways. Diseases included in this category are rhinitis, asthma, bronchitis, pneumonitis, interstitial pulmonary fibrosis, and a number of other inflammatory lung diseases that might respond to inhibition of IL-1 activity. It has been demonstrated that lung cells and airways represent an area where significant amounts of IL-1$\beta$ are generated during inflammatory reactions.

MATERIALS AND METHODS

Plasmid Constructions

Figure 1:
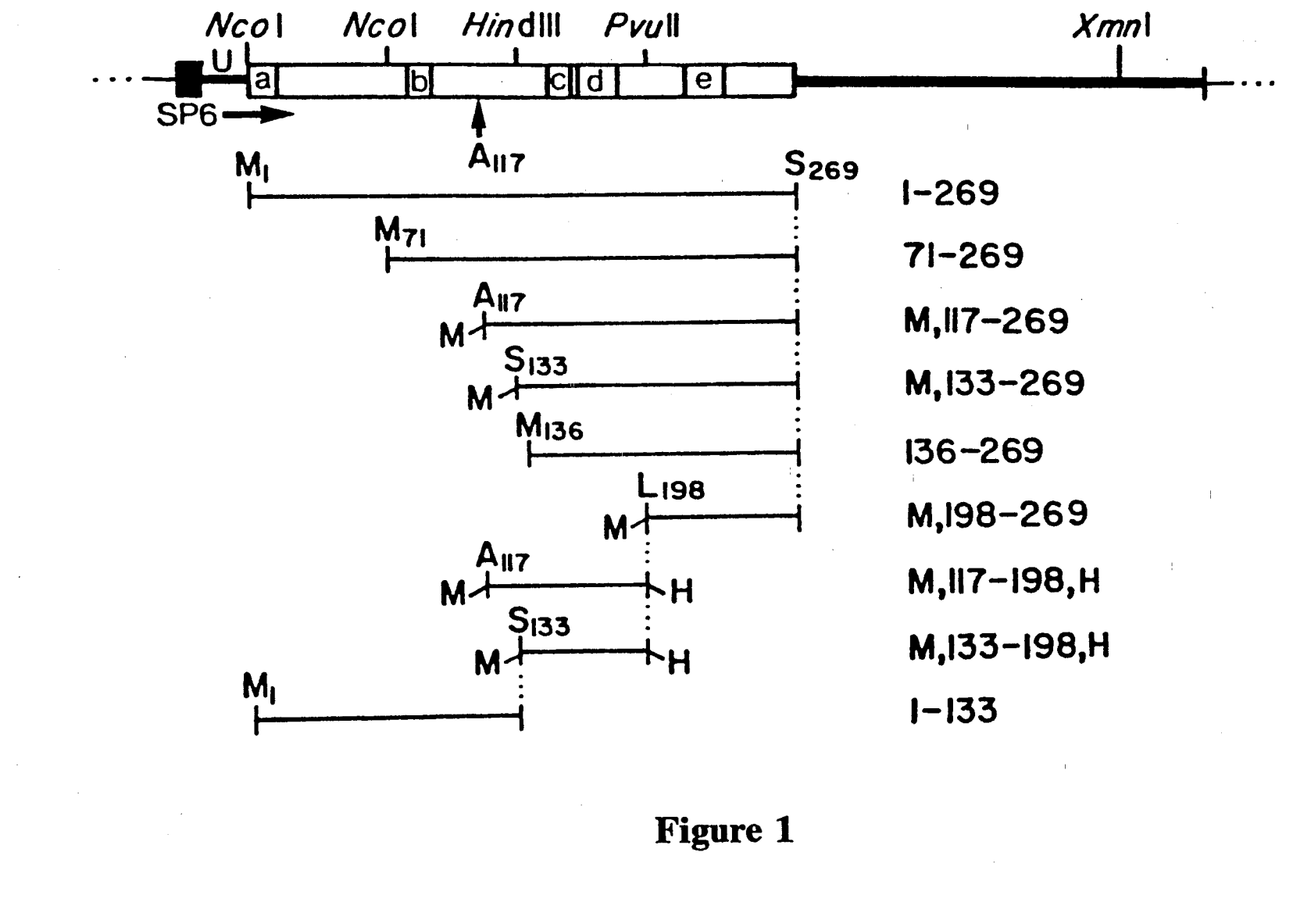

The plasmid constructs used to generate IL-1$\beta$ mRNAs for in vitro translation are diagrammed in FIG. 1. The IL-1$\beta$ cDNA was subcloned into plasmid pSP64 (Promega Biotec), and the 86-base pair IL-1$\beta$ mRNA untranslated leader (UTL) sequence was excised and replaced with the 37-base pair UTL of alfalfa mosaic virus RNA 4. As described elsewhere (Jobling, S. A., and L. Gehrke [1987] Nature 325:622-625), the translational efficiency of the IL-1$\beta$ mRNA is increased by replacing the native UTL with that of the plant viral RNA. The noncoding AMV RNA 4 UTL oligonucleotide was ligated to the IL-1$\beta$ cDNA at the NcoI site (CCATGG) situated at the initiating ATG codon; therefore, the amino acid sequence of proIL-1$\beta$ is not altered. Deletion constructs were generated principally by cleaving the IL-1$\beta$ cDNA sequence at the restriction enzyme sites shown in FIG. 1, followed by ligation of the termini to maintain the translational reading frame. The numbers to the right of FIG. 1 refer to amino acid positions, using proIL-1$\beta$ (269 amino acids) as reference. In some of the constructs, it was necessary to add a methionine (ATG) codon to initiate translation, and the added methionine is noted in the label and separated from the numbered amino acid positions (e.g., M, 117-269). In two constructs (FIG. 1, lower), an added histidine residue precedes the termination codon, and notation similar to that described above is used in the label. The IL-1-(M, 117-269) construct was generated by ligating a synthetic 60-base pair oligonucleotide at the HindIII site of the IL-1$\beta$ cDNA. With the exception of SP6 IL-1$\beta$, all messenger RNAs transcribed from the constructs shown in FIG. 1 contain the alfalfa mosaic virus RNA 4 UTL.

Transcription of IL-1$\beta$ Plasmid DNAs

Plasmid DNAs were linearized with BamHI and transcribed as described previously (Jobling & Gehrke [1987], supra).

In Vitro Translations

Capped SP6 mRNAs were transcribed from linearized DNAs, and low molecular-weight materials were removed by passing the DNAse-treated transcription reaction through two successive Sephadex G-50 spun columns. The eluate was then extracted twice with phenol/chloroform, once with ether, and nucleic acids were precipitated with ethanol from 2.5M ammonium acetate. Translations were performed essentially according to the manufacturer's recommendations. Wheat-germ translations were prepared using 5 $\mu$l of nuclease-treated wheat-germ extract (Amersham) in a total volume of 10 $\mu$l containing 105 mM potassium acetate, 2 mCi ml$^{-1}$ $^{35}$S-methionine, and the reaction mixture was incubated for 1 hour at 30° C.

Following are examples which illustrate procedures, including the best mode, for practicing the invention. These examples should not be construed as limiting. All percentages are by weight and all solvent mixture proportions are by volume unless otherwise noted.

EXAMPLE 1

Synthesis of IL-1$\beta$ Proteins

The IL-1$\beta$ proteins were synthesized by in vitro translation of SP6 or T7 messenger RNAs. In vitro protein synthesis was performed as described previously (Jobling et al., 1988; Jobling, S. A., and L. Gehrke [1987] Nature 325:622-625). The translational efficiency of all construct mRNAs was increased by replacing the untranslated leader sequence of the IL-1$\beta$ mRNA with that of alfalfa mosaic virus RNA (Jobling et al., 1988; Jobling et al., 1987). All IL-1$\beta$ protein translation products contain the amino-terminal methionine residue added during initiation of protein synthesis. The biological activity of the translation products was tested by quantitating [$^3$H]thymidine incorporation by helper T-cells (D10.G4.1) (Kaye, Y., S. Porcelli, J. Tite, B. Jones, C. A. Janeway [1983] J. Exp. Med. 158:836-856) incubated in the presence of diluted translation reaction mixtures (FIG. 2). The results demonstrate that the half maximal biological activity of the Arg$_{127}$→Gly$_{127}$ mutant protein is greater than that of proIL-1$\beta$, but at least 100-fold less than that of the wild-type mature IL-1$\beta$.

EXAMPLE 2

Receptor Binding Characteristics

Figure 3:
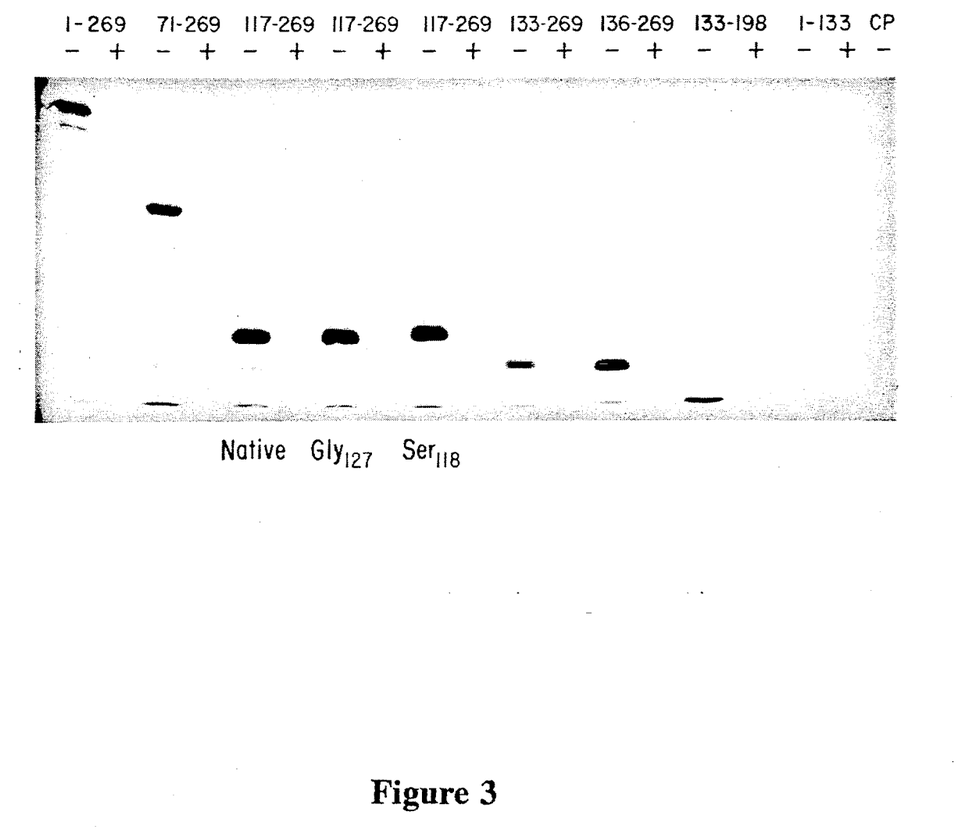

The receptor binding characteristics of the Arg$_{127}$→Gly$_{127}$ mutant protein were determined by Scatchard analysis and by sodium dodecyl sulfate (SDS) polyacrylamide gel analysis of specifically bound proteins (Dower et al., 1986; Jobling et al., 1988; Mosley et al., J. Biol. Chem. 1987). For the polyacrylamide gel analysis, IL-1$\beta$ proteins were labeled with [$^{35}$S]methionine during in vitro translation before cell surface receptor binding assays using EL4 6.1 C10 murine thymoma cells (Jobling et al., 1988; Mosley et al., Proc. Natl. Acad. Sci. USA, 1987; MacDonald, H. R., R. K. Lees, C. Bron [1985] J. Immunol. 135:3944) (FIG. 3). The intensity of the bands representing bound native mature IL-1$\beta$ and bound Arg$_{127}$→Gly$_{127}$ mutant IL-1$\beta$ (FIG. 3) suggested that the receptor binding properties were similar despite the observation that the bioactivities of the proteins were unequal (FIG. 2). Equilibrium binding experiments and Scatchard plot data (Table 1) confirmed the equivalence of binding constants.

Figure 4:
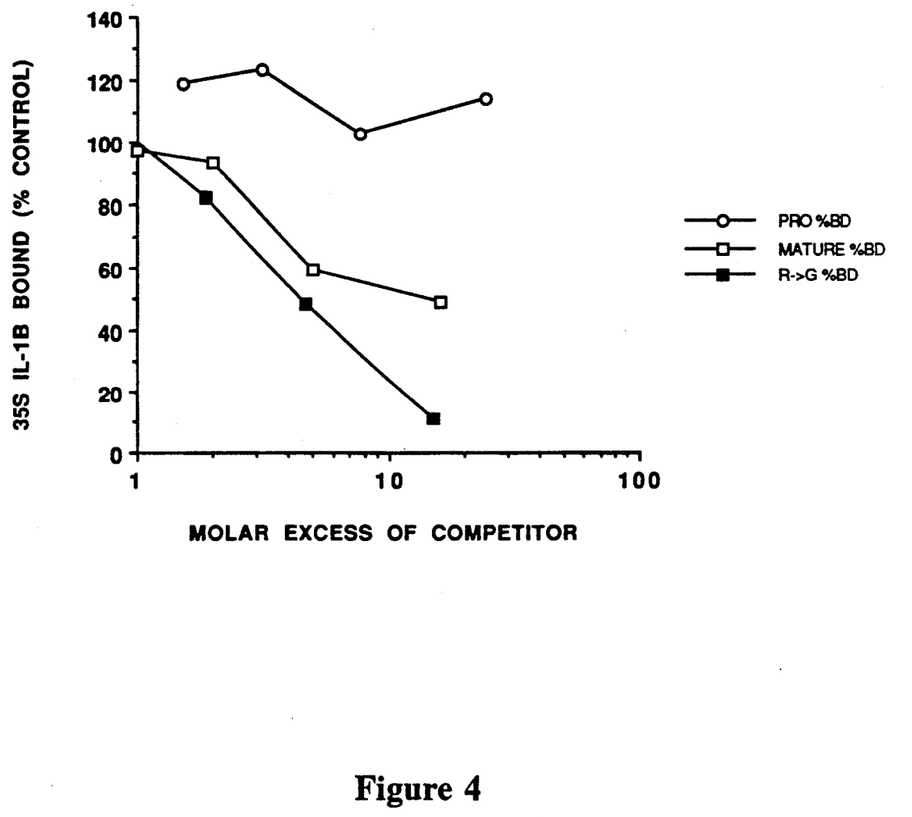

As a further analysis of the receptor binding properties, nonradioactive proteins were used to complete with [$^{35}$S]-labeled wild-type mature IL-1$\beta$ for binding to EL4 cell receptors (FIG. 4). Competitive receptor binding was performed by incubating EL.4 thymoma cells at 37° C. in the presence of a constant level of [$^{35}$S]-labeled mature IL-1$\beta$ protein and increasing concentrations of non-radioactive IL-1$\beta$ competitor translation products. Reticulocyte lysate translation reaction mixtures were passed through Sephadex G-50 spun columns to remove unincorporated [$^{35}$S]methionine before incubation with cells (Mosley et al., J. Biol. Chem., 1987). 1.9×10$^7$ EL.4 cells were incubated in 250 ul binding medium (RPMI 1640 medium containing 1% bovine serum albumin, 20 mM HEPES, pH 7.4, and 0.1% sodium azide) with increasing amounts of IL-1β translation products. The amount of IL-1β protein synthesized by in vitro translation was determined by specific radioactivity using a radioactive IL-1β protein standard which was quantitated by radioimmune assay. Following incubation at 37° C. in the presence or absence of unlabeled competitor, free and bound proteins were separated by pelleting the cells through silicone fluid (Jobling et al., 1988). The cells were solubilized in lysis buffer (50 mM sodium phosphate, pH 7; 10 mM ethylenediaminetetraacetic acid (EDTA); 0.1% TRITON ™ X-100; 0.1% sarkosyl; 10 mM β-mercaptoethanol) before quantitation of bound radioactivity by liquid scintillation counting. The equilibrium binding data suggested equal binding constants for wild-type IL-1β and the $Arg_{127} \rightarrow Gly_{127}$ mutant protein (Table 1); therefore, we expected these proteins to block [$^{35}$S]IL-1β binding with similar kinetics. The affinity of proIL-1β for receptor is 30-fold less than that of the mature (Jobling et al., 1988), and this protein was not expected to compete effectively with wild-type mature IL-1β for cellular receptors. The data (FIG. 4) demonstrate that at concentrations up to a five-fold molar excess, the unlabeled wild-type mature IL-1β and the $Arg_{127} \rightarrow Gly_{127}$ mutant IL-1β protein reproducibly competed more effectively than the wild-type mature IL-1β. As anticipated, proIL-1β protein competed minimally at these concentrations. The SDS-gel analysis of bound protein (FIG. 3), the equilibrium binding data (Table 1), and competition binding experiments (FIG. 4) support the conclusion that the receptor binding affinity of the $Arg_{127} \rightarrow Gly_{127}$ mutant IL-1β protein is unaffected while biological activity is greatly reduced (FIG. 2).

We claim:

1. A mutein of a biologically active IL-1β protein wherein said mutein has substantially reduced IL-1β activity but does bind to an IL-1β receptor, and wherein the mutein comprises an amino acid substitution wherein the arginine residue corresponding to position 11 of the mature form of IL-1β, or position 127 of the precursor, is replaced with glycine.

2. The mutein, according to claim 1, wherein said mutein is in the precursor form.

3. The mutein, according to claim 1, which is in the mature form.

4. A process for binding a protein to IL-1β receptors without resulting in substantial IL-1β activity, said process comprising delivery to IL-1β receptors of an effective amount of a mutein of an IL-1β protein which has a substantially reduced level of biological activity as compared to the corresponding native IL-1β but which binds to IL-1β receptors, wherein said mutein has glycine substituted in place of the arginine residue which naturally occurs at position 11 of the mature form, or position 127 of the precursor form, of IL-1β.

5. The process, according to claim 3, wherein said mutein is in the precursor form.

6. The process, according to claim 3, wherein said mutein is in the mature form.

* * * * *

UNITED STATES PATENT AND TRADEMARK OFFICE
CERTIFICATE OF CORRECTION

PATENT NO. : 5,286,847
DATED : February 15, 1994
INVENTOR(S) : Lee Gehrke, et. al.

It is certified that error appears in the above-indentified patent and that said Letters Patent is hereby corrected as shown below:

Column 1    line 54:  Delete "thr-met-val-arg-ser" and insert --thr-met-val-arg-ser--.

Column 1    line 56:  Delete "val-glu-ser" and insert --val-glu-ser--

Column 3    line 33:  After "precursor" insert --)--.

Column 3    line 47 (Table 1):  Delete "$Arg_{12}$" and insert --$Arg_{127}$--.

Column 4    lines 26-27:  Delete "comparative" and insert --competitive--.

Column 8    line 26:  Delete "claim 3" insert --claim 4--.

Column 8    line 28:  Delete "claim 3" and insert --claim 4--.

Signed and Sealed this

Twenty-eighth Day of June, 1994

Attest:

BRUCE LEHMAN

Attesting Officer      Commissioner of Patents and Trademarks